United States Patent
Wager

(10) Patent No.: US 7,300,943 B2
(45) Date of Patent: *Nov. 27, 2007

(54) GSK-3 INHIBITORS

(75) Inventor: Travis T. Wager, New London, CT (US)

(73) Assignee: Pfizer Inc., New York, NY (US)

( * ) Notice: Subject to any disclaimer, the term of this patent is extended or adjusted under 35 U.S.C. 154(b) by 484 days.

This patent is subject to a terminal disclaimer.

(21) Appl. No.: 10/874,962

(22) Filed: Jun. 23, 2004

(65) Prior Publication Data

US 2005/0026946 A1   Feb. 3, 2005

Related U.S. Application Data

(60) Provisional application No. 60/483,489, filed on Jun. 27, 2003.

(51) Int. Cl.
*A61K 31/47*   (2006.01)
*C07D 471/04*   (2006.01)

(52) U.S. Cl. .................................. 514/303; 546/119
(58) Field of Classification Search ............... 546/119; 514/303
See application file for complete search history.

(56) References Cited

U.S. PATENT DOCUMENTS 4,020,072 A   4/1977   Hoehn .................... 260/293.6

FOREIGN PATENT DOCUMENTS

| DE | 138773 | 11/1979 |
|---|---|---|
| WO | WO 0224694 | 3/2002 |
| WO | WO 03045949 | 6/2003 |

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

Quiroga et al 'Synthesis, molecular structure and tautomerism of 1(2)H-dihydropyrazolo[3,4-b]pyridin-6-ones' CA 131:116184 (1999).*

Dorn, H. et al., Journal f. prakt. Chemie. Band, vol. 324, pp. 557-562, Heft 4, 1982, "Eindeutige Synthese des 4,7-Dihydro-4-oxo-1H-pryzolo[3,4-b]pyridins Bemerkungen zur,,(N-C)-Umlagerung von (2-Alkoxycarbonyl-vinly-amino)pyrazolen".

Ibrahim, M.K.A. et al., J. Indian Chem. Soc., vol. 74, pp. 206-208, Mar. 1977, "Synthesis of Pyrazoles and Fused Pyrazoles. Novel Synthesis of Pyrano[2,3-c]pyrazole, Thieno[2,3-c]pyrazole and Pyrazolo[3,4-b]pyridine Derivatives".

Balicki, Roman, Polish Journal of Chemistry, Part X, vol. 56, 1273, pp. 789-797, 1983, "Studies in the Field of Nitrogen Heterocyclic Compounds. Part XI*. Abnormal Cyclocondensation of Ethyl 4,4,4-Trifluoroacetoacetate with Aminopyrazoles".

* cited by examiner

*Primary Examiner*—Bernard Dentz
(74) *Attorney, Agent, or Firm*—Ye Hua; Stephen D. Prodnuk; Bryan C. Zielinski

(57) ABSTRACT

The invention provides compounds of formula (I)

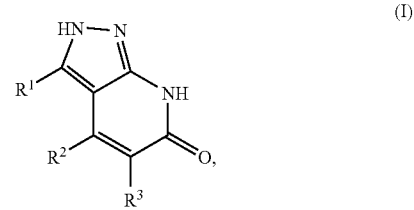

the stereoisomers and prodrugs thereof, and the pharmaceutically acceptable salts of the compounds, stereoisomers, and prodrugs, wherein $R^1$, $R^2$, and $R^3$ are as defined herein; pharmaceutical compositions thereof; and use thereof in the treatment of, inter alia, conditions, diseases, and symptoms such as diabetes, dementia, Alzheimer's Disease, stroke, schizophrenia, depression, hair loss, and cancer.

6 Claims, No Drawings

GSK-3 INHIBITORS

This application claims priority to U.S. Provisional Application Ser. No. 60/483,489, filed Jun. 27, 2003.

FIELD OF THE INVENTION

The invention relates to substituted pyrazolo[3,4-b]pyridin-6-ones which are inhibitors of cyclin-dependent protein kinase-2 (cdk-2), cyclin-dependent protein kinase-5 (cdk-5), and glycogen synthase kinase 3 (GSK-3). As such, they are useful in the treatment of, inter alia, conditions, diseases, and symptoms such as diabetes, dementia, Alzheimer's Disease, stroke, schizophrenia, depression, hair loss, and cancer.

BACKGROUND OF THE INVENTION

The serine/threonine kinase cdk-2 is essential for normal cellular cycling and plays a critical role in disorders arising from abnormal cell cycling, a common characteristic of many oncological disorders. Inhibitors of cdk-2 are therefore useful in the treatment of various types of cancers and other diseases or conditions related to abnormal cell growth. See, for example, Meijer, et al., Pharmacol. and Therapeutics, 82 (2-3), 279-284 (1999), Sausville, et al., Pharmacol. and Therapeutics, 82 (2-3), 285-292 (1999). The serine/threonine kinase cdk-5, along with its cofactor p25, or the longer cofactor p35, has been linked to neurodegenerative disorders, and inhibitors of cdk-5 are therefore useful in the treatment of disorders such as Alzheimer's Disease, Parkinson's Disease, stroke, and Huntington's Disease. Treatment of such neurodegenerative disorders using cdk-5 inhibitors is supported by the finding that cdk-5 is involved in the phosphorylation of tau protein, and dopamine and cyclic AMP-regulated phosphoprotein (DARPP-32) at threonine 75, and is thus indicated as playing a role in dopaminergic transmission.

Glycogen synthase kinase-3 (GSK-3), a proline-directed, serine/threonine kinase for which two isoforms, GSK-3α and GSK-3β, have been identified, phosphorylates the rate-limiting enzyme of glycogen synthesis, glycogen synthase (GS). See, for example, Embi, et al., Eur. J. Biochem., 107, 519-527 (1980). GSK-3α and GSK-3β are both highly expressed in the body. See, for example, Woodgett, et al., EMBO, 9, 2431-2438 (1990) and Loy, et al., J. Peptide Res., 54, 85-91 (1999). Besides GS, a number of other GSK-3 substrates have been identified, including many metabolic, signaling, and structural proteins. Notable among the plurality of signaling proteins regulated by GSK-3 are many transcription factors, including activator protein-1; cyclic AMP response element binding protein (CREB); the nuclear factor (NF) of activated T-cells; heat shock factor-1; β-catenin; c-Jun; c-Myc; c-Myb; and NF-$_{KB}$. See, for example, C. A. Grimes, et al., Prog. Neurobiol., 65, 391-426 (2001), H. Eldar-Finkelman, Trends in Molecular Medicine, 8, 126-132 (2002), and P. Cohen, et al., Nature, 2, 1-8, (2001). Accordingly, targeting the activity of GSK-3 has significant therapeutic potential in the treatment of many disparate pathologies and conditions, for example, Alzheimer's Disease (A. Castro, et al., Exp. Opin. Ther. Pat., 10, 1519-1527 (2000)); asthma (P. J. Barnes, Ann. Rev. Pharmacol. Toxicol., 42, 81-98 (2002)); cancer (Beals, et al., Science, 275, 1930-1933 (1997), L. Kim, et al., Curr. Opin. Genet. Dev., 10, 508-514 (2000), and Q. Eastman, et al., Curr. Opin. Cell Biol., 11, 233 (1999)); diabetes and its related sequelae, for example, Syndrome X and obesity (S. E. Nikoulina, et al., Diabetes, 51, 2190-2198 (2002), Orena, et al., JBC, 15765-15772 (2000), and Summers, et al., J. Biol. Chem., 274 17934-17940 (1999)); hair loss (S. E. Millar, et al., Dev. Biol., 207, 133-149 (1999) and E. Fuchs, et al., Dev. Cell, 1, 13-25 (2001)); inflammation (P. Cohen, Eur. J. Biochem., 268, 5001-5010 (2001)); mood disorders, such as depression (A. Adnan, et al., Chem. Rev., 101, 2527-2540 (2001) and R. S. B. Williams, et al., Trends Phamacol. Sci., 21, 61-64 (2000)); neuronal cell death and stroke (D. A. E. Cross, et al., J. Neurochem., 77, 94-102 (2001) and C. Sasaki, et al., Neurol. Res., 23, 588-592 (2001)); bipolar disorder (Klein, et al., PNAS, 93, 8455-8459 (1996)); skeletal muscle atrophy (G. J. Brunn, et al., Science, 277, 99-101 (1997), R. E. Rhoads, J. Biol. Chem., 274, 30337-30340 (1999), V. R. Dharmesh, et al., Am. J. Physiol. Cell Physiol. 283, C545-551 (2002), and K. Baar, et al., A. J. Physiol., 276, C120-C127 (1999)); decreased sperm motility (Vijayaraghavan, et al., Biol. Reproduction, 54, 709-718 (1996)); and in cardio-protection (C. Badorff, et al., J. Clin. Invest., 109, 373-381 (2002), S. Haq, et al., J. Cell Biol., 151, 117-129 (2000), and H. Tong, et al., Circulation Res., 90, 377-379 (2002)).

SUMMARY OF THE INVENTION

The invention provides compounds of formula (I)

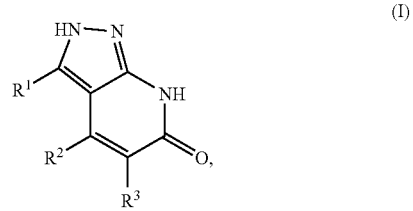

the stereoisomers and prodrugs thereof, and the pharmaceutically acceptable salts of the compounds, stereoisomers, and prodrugs, wherein $R^1$, $R^2$, and $R^3$ are as defined herein; pharmaceutical compositions thereof; and use thereof in the treatment of, inter alia, conditions, diseases, and symptoms such as diabetes, dementia, Alzheimer's Disease, stroke, schizophrenia, depression, hair loss, and cancer.

DETAILED DESCRIPTION OF THE INVENTION

The present invention relates to compounds of formula (I)

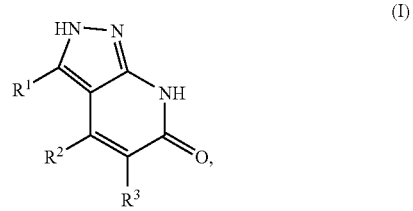

the stereoisomers and prodrugs thereof, and the pharmaceutically acceptable salts of the compounds, stereoisomers, and prodrugs, wherein:

$R^1$ and $R^2$ are, independently, hydrogen; —($C_1$-$C_8$)alkyl; —($C_1$-$C_8$)alkoxy; —($C_3$-$C_{11}$)cycloalkyl; heterocycloalkyl; aryl; or heteroaryl; and $R^3$ is hydrogen; —$(C_1$-$C_8)$alkyl; —$(C_1$-$C_8)$alkoxy; or —$(C_3$-$C_{11})$cycloalkyl;

wherein each $R^1$, $R^2$, and $R^3$ is optionally, and independently, substituted with from one to six of: (A) halogen; (B) aryl, optionally substituted with from one to three of: (i) —OH; (ii) —CN; (iii) halogen; (iv) heteroaryl; (v) —$CH_2OR^4$; or (vi) —$CH_2NR^4R^5$; (C) heteroaryl; (D) —$NO_2$; (E) —CN; (F) —$(C_1$-$C_8)$alkyl, optionally substituted with from one to three halogen atoms; (G) —$(C_1$-$C_8)$thioalkoxy; (H) —$NR^4R^5$; (I) —$NR^4C(=O)R^5$; (J) —$NR^4C(=O)NR^4R^5$; (K) —$NR^4(SO_2)R^5$; (L) —$NR^4(SO_2)NR^4R^5$; (M) —$OR^4$; (N) —$OC(=O)R^4$; (O) —$OC(=O)OR^4$; (P) —$C(=O)OR^4$; (Q) —$C(=O)R^4$; (R) —$C(=O)NR^4R^5$; (S) —$OC(=O)NR^4R^5$; (T) —$OC(=O)SR^4$; (U) —$SR^4$; (V) —$S(=O)R^4$; (W) —$SO_2R^4$; or (X) —$SO_2R^4R^5$; wherein:

$R^4$ and $R^5$ are, independently, hydrogen; aryl, optionally substituted with from one to three of: halogen; —OH; —$(C_1$-$C_8)$alkyl, optionally substituted with aryl; or —$C_3$-$C_{11})$cycloalkyl;

provided that when $R^3$ is hydrogen: (1) $R^1$ is not hydrogen, and $R^2$ is not hydrogen or methyl; (2) $R^1$ and $R^2$ are not both methyl; or (3) $R^1$ is not hydrogen or phenyl, and $R^2$ is not trifluoromethyl.

A generally preferred subgroup of the compounds of formula (I) comprises those compounds wherein:

$R^1$ is —$(C_1$-$C_5)$alkyl or —$(C_3$-$C_6)$cycloalkyl;

$R^2$ is hydrogen; —$(C_1$-$C_8)$alkyl; —$(C_1$-$C_8)$alkoxy; —$(C_3$-$C_9)$cycloalkyl; heterocycloalkyl; aryl; or heteroaryl; and $R^3$ is hydrogen; —$(C_1$-$C_3)$alkyl; —$(C_1$-$C_6)$alkoxy; or —$(C_3$-$C_6)$cycloalkyl;

wherein each $R^1$, $R^2$, and $R^3$ is optionally, and independently, substituted with from one to six of: (A) halogen; (B) aryl, optionally substituted with from one to three of: (i) —OH; (ii) —CN; (iii) halogen; (iv) heteroaryl; (v) —$CH_2OR^4$; or (vi) —$CH_2NR^4R^5$; (C) heteroaryl; (D) —$NO_2$; (E) —CN; (F) —$(C_1$-$C_8)$alkyl, optionally substituted with from one to three fluorine atoms; (G) —$(C_1$-$C_8)$thioalkoxy; (H) —$NR^4R^5$; (I) —$NR^4C(=O)R^5$; (J) —$NR^4C(=O)NR^4R^5$; (K) —$NR^4(SO_2)R^5$; (L) —$NR^4(SO_2)NR^4R^5$; (M) —$OR^4$; (N) —$OC(=O)R^4$; (O) —$OC(=O)OR^4$; (P) —$C(=O)OR^4$; (Q) —$C(=O)R^4$; (R) —$C(=O)NR^4R^5$; (S) —$OC(=O)NR^4R^5$; (T) —$OC(=O)SR^4$; (U) —$SR^4$; (V) —$S(=O)R^4$; (W) —$SO_2R^4$; or (X) —$SO_2R^4R^5$.

Another generally preferred subgroup of the compounds of formula (I) comprises those compounds wherein:

$R^1$ is —$(C_1$-$C_5)$alkyl or —$(C_3$-$C_6)$cycloalkyl;

$R^2$ is hydrogen; —$(C_1$-$C_8)$alkyl; —$(C_1$-$C_8)$alkoxy; —$(C_3$-$C_9)$cycloalkyl; heterocycloalkyl; aryl; or heteroaryl; and $R^3$ is hydrogen;

wherein each $R^1$ or $R^2$ is optionally, and independently, substituted with from one to six of: (A) Cl or Fl; (B) aryl, optionally substituted with from one to three of: (i) —OH; (ii) —CN; (iii) halogen; (iv) heteroaryl; (v) —$CH_2OR^4$; or (vi) —$CH_2NR^4R^5$; (C) heteroaryl; (E) —CN; (F) —$CF_3$; (G) —$(C_1$-$C_8)$thioalkoxy; (H) —$NR^4R^5$; (I) —$NR^4C(=O)R^5$; (J) —$NR^4C(=O)NR^4R^5$; (K) —$NR^4(SO_2)R^5$; (L) —$NR^4(SO_2)NR^4R^5$; (M) —$OR^4$; (N) —$OC(=O)R^4$; (O) —$OC(=O)OR^4$; (P) —$C(=O)OR^4$; (Q) —$C(=O)R^4$; (R) —$C(=O)NR^4R^5$; (S) —$OC(=O)NR^4R^5$; (T) —$OC(=O)SR^4$; (W) —$SO_2R^4$; or (X) —$SO_2R^4R^5$.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix $(C_a$-$C_b)$alkyl indicates an alkyl moiety of the integer "a" to "b" carbon atoms, inclusive.

The term "alkoxy" refers refers to straight or branched, monovalent, saturated aliphatic chains of carbon atoms bonded to an oxygen atom, wherein the alkoxy group optionally incorporates one or more double or triple bonds, or a combination of double bonds and triple bonds. Examples of alkoxy groups include methoxy, ethoxy, propoxy, butoxy, iso-butoxy, tert-butoxy, and the like.

The term "alkyl" refers to straight, or branched, monovalent chains of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, 2-butynyl, and the like.

The term "aryl" denotes a cyclic, aromatic hydrocarbon. Examples of aryl groups include anthracenyl, fluorenyl, phenanthrenyl, phenyl, naphthyl, and the like.

The term "cycloalkyl" denotes a saturated monocyclic, or polycyclic, cycloalkyl group, optionally fused to an aryl group, wherein the cycloalkyl group optionally incorporates one or more double or triple bonds, or a combination of double bonds and triple bonds, but which is not aromatic. Examples of cycloalkyl groups include adamantanyl, cyclopropyl, cyclobutyl, cyclopentyl, cyclohexyl, cycloheptyl, decahydronaphthalinyl, norbornanyl, and the like.

The term "halogen" represents chloro, fluoro, bromo, and iodo.

The term "heteroaryl" denotes a monocyclic or polycyclic aromatic hydrocarbon group wherein one or more carbon atoms have been replaced with heteroatoms selected from the group consisting of nitrogen, oxygen, and sulfur. If the heteroaryl group contains more than one heteroatom, the heteroatoms may be the same or different. Examples of heteroaryl groups include benzofuranyl, benzothienyl, benzimidazolyl, benzoxazolyl, benzothiazolyl, chromenyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated monocyclic or polycyclic cycloalkyl group, optionally fused to an aromatic or heteroaromatic hydrocarbon group, in which at least one of the carbon atoms has been replaced with a heteroatom selected from the group consisting of nitrogen, oxygen, and sulfur. If the heterocycloalkyl group contains more than one heteroatom, the heteroatoms may be the same or different. Examples of such heterocycloalkyl groups include azabicycloheptanyl, azetidinyl, benzazepinyl, 1,3-dihydroisoindolyl, dioxanyl, carbazolyl, dioxolanyl, dithianyl, indolinyl, imidazolidinyl, morpholinyl, quinuclidinyl, phenoxazinyl, piperazinyl, piperidyl, pyrazolidinyl, pyrrolidinyl, tetrahydrofuryl, tetrahydroindolyl, tetrahydroisoquinolinyl, tetrahydropyranyl, tetrahydroquinolinyl, tetrahydroquinoxalinyl, tetrahydrothiopyranyl, tetrahydro-2H-1,4-thiazinyl, thiazolidinyl, thiomorpholinyl, thioxanthenyl, thioxanyl, trithianyl, and the like.

The term "thioalkoxy" denotes an alkoxy group, as defined hereinabove, wherein a sulfur atom has been substituted for the oxygen atom.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the preparation and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e. g., an organic radical is a group of atoms that imparts characteristic properties to a compound containing it, or which remains unchanged during a series of reactions, or transformations.

The term "salts" refers to organic and inorganic salts of a compound of formula (I), or a stereoisomer, or prodrug thereof. These salts can be prepared in situ during the final isolation and purification of a compound, or by separately reacting a compound of formula (I), or a stereoisomer or prodrug thereof, with a suitable organic or inorganic acid or base and isolating the salt thus formed. Representative salts include, but are not limited to, the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The term "substituted" means that a hydrogen atom on a molecule has been replaced with a different atom or molecule. The atom or molecule replacing the hydrogen atom is denoted as a "substituent."

The symbol "-" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended, unless specified otherwise, that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond, both the cis- and trans-forms, as well as mixtures thereof, are embraced within the scope of the invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Also, some of the compounds of formula (I) may be atropisomers (e.g., substituted biaryls) and are also considered as part of the invention.

The compounds of formula (I) may exist in unsolvated as well as solvated forms with pharmaceutically acceptable solvents, such as water, ethanol, and the like, and it is intended that the invention embrace both solvated and unsolvated forms.

The compounds of formula (I) may exist as tautomeric mixtures in equilibrium, represented hereinbelow by formulae (I) and (Ia). Although, for illustrative convenience, the compounds of the present invention are depicted as comprising the tautomer of formula (I), both tautomeric forms (I) and (Ia) are intended to be embraced within the scope of the invention.

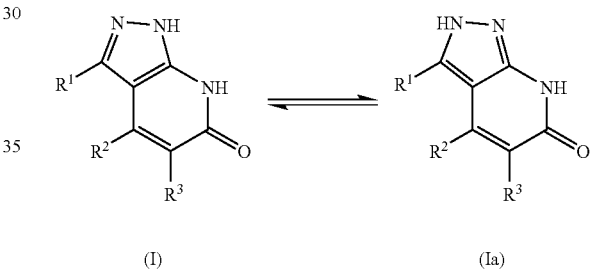

(I)                              (Ia)

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The compounds of formula (I), the stereoisomers and prodrugs thereof, and the pharmaceutically acceptable salts of the compounds, stereoisomers, or prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their relative ease of preparation and facile detection. Furthermore, substitution with heavier isotopes such as deuterium, i.e., $^2H$, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Scheme and/or Examples set forth hereinbelow, by substituting an isotopically-labeled reagent for a non-isotopically-labeled reagent.

In another aspect, the invention provides methods of treating glycogen synthase kinase-3-mediated conditions, diseases, or symptoms in a mammal in need of such treatment which methods comprise administering to a mammal in need of such treatment a therapeutically effective amount of a compound of formula (I), a prodrug thereof, or a pharmaceutically acceptable salt of the compound or prodrug; a pharmaceutical composition comprising a compound of formula (I), a prodrug thereof, or a pharmaceutically acceptable salt of the compound or prodrug, and a pharmaceutically acceptable carrier, vehicle, or diluent; or a combination of an amount of a compound of formula (I), a prodrug thereof, or a pharmaceutically acceptable salt of the compound or prodrug, and an amount of one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator; or a pharmaceutical composition comprising the aforementioned combinations.

Preferred conditions, diseases, and symptoms treatable according to the instant methods are those selected from the group consisting of Alzheimer's Disease, asthma, atherosclerosis, anxiety, bipolar disorder, cancer, diabetes, dementia, depression, frailty, hair loss, heart failure, essential hypertension, hyperglycemia, hyperlipidemia, hypoglycemia, inflammation, ischemia, mood disorders, neuronal cell death, obesity, obsessive compulsive disorder, polycystic ovary disorder, schizophrenia, stroke, Syndrome X, and traumatic brain injury.

Frailty is characterized by the progressive and relentless loss of skeletal muscle mass resulting in a high risk of injury from fall, difficulty in recovery from illness, prolongation of hospitalization, and long-term disability requiring assistance in daily living. The reduction of muscle mass and physical strength typically leads to diminished quality of life, loss of independence, and mortality. Frailty is normally associated with aging, but may also result when muscle loss and reduced strength occur due to other factors, such as disease-induced cachexia, immobilization, or drug-induced sarcopenia. Another term that has been used to denote frailty is sarcopenia, which is a generic term for the loss of skeletal muscle mass, or quality. Examples of skeletal muscle properties that contribute to its overall quality include contractility, fiber size and type, fatiguability, hormone responsiveness, glucose uptake/metabolism, and capillary density.

Generally preferred anti-angiogenesis agents may comprise, for example, matrix metalloproteinase-2 (MMP-2) inhibitors, matrix metalloproteinase-9 (MMP-9) inhibitors, and cyclooxygenase-II (COX-II) inhibitors. Examples of useful MMP-2 and MMP-9 inhibitors are disclosed in, for example, PCT International Application Publication Nos. WO 98/34915 and WO 98/34918, and U.S. Pat. Nos. 5,240, 958; 5,310,763; 5,455,258; 5,506,242; 5,530,161; 5,552, 419; 5,672,615; 5,861,510; 5,863,949; 5,932,595; 5,994, 351; 6,077,864; 6,087,392; 6,090,852; 6,110,964; 6,147, 061; 6,147,074; 6,303,636; 6,380,219; and 6,387,931. Examples of COX-II inhibitors useful in the present combinations and methods comprise CELEBREX® (celecoxib, U.S. Pat. No. 5,466,823), valdecoxib (U.S. Pat. No. 5,633, 272), and rofecoxib (U.S. Pat. No. 5,474,995). Generally preferred MMP-2 and MMP-9 inhibitors are those that exhibit little or no activity inhibiting MMP-1. Especially preferred MMP-2 and MMP-9 inhibitors are those that selectively inhibit MMP-2 and/or MMP-9 relative to other MMP inhibitors, i.e., MMP-1, MMP-3, MMP-4, MMP-5, MMP-6, MMP-7, MMP-8, MMP-10, MMP-11, MMP-12, and MMP-13. Specific examples of MMP inhibitors useful in the combinations and methods of the instant invention comprise AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonyl-amino]-8-oxa-bicyclo[3.2.1]octane-3-carboxylic acid hydroxamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonyl-amino]-tetrahydro-pyran-4-carboxlyic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonyl-amino]-tetrahydro-pyran-4-carboxlyic acid hydroxyamide;

(R)-3-[4-(4-chloro-phenoxy)-benzenesulfonyl-amino]-tetrahydro-pyran-3-carboxlyic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonyl-amino]-8-oxa-bicyclo[3.2.1]octane-3-carboxylic acid hydroxamide;

3-endo-3-[4-(4-fluoro-phenoxy)-benzenesulfonyl-amino]-8-oxa-bicyclo[3.2.1]octane-3-carboxylic acid hydroxamide; and (R)-3-[4-(4-fluoro-phenoxy)-benzenesuffonyl-amino]-tetrahydro-furan-3-carboxylic acid hydroxyamide; and the pharmaceutically acceptable salts and solvates thereof.

Generally preferred signal transduction inhibitors may comprise, for example, epidermal growth factor receptor (EGFR) response inhibitors, such as EGFR antibodies, EGF antibodies, and molecules that are EGFR inhibitors; vascular endothelial growth factor (VEGF) inhibitors; and erbB2 receptor inhibitors, such as molecules or antibodies that bind to the erbB2 receptor, for example, HERCEPTIN® (Genentech Inc.; South San Francisco, Calif.). EGFR inhibitors are described in, for example, PCT International Application Publication No. WO 98/14451, and U.S. Pat. Nos. 5,679, 683; 5,747,498; and 6,391,874. EGFR-inhibiting agents may comprise, for example, the monoclonal antibodies C225 and anti-EGFR 22Mab (Imclone Systems, Inc.), ZD-1839, BIBX-1382, MDX-103, VRCTC-310, and EGF fusion toxin (Seragen Inc.; Hopkinton, Mass.). VEGF inhibitors are disclosed in, for example, PCT International Application Publication No. WO 99/24440, and U.S. Pat. Nos. 5,792, 783; 5,834,504; 5,851,999; 5,883,113; 5,886,020; 6,051, 593; 6,114,371; 6,133,305; 6,162,804; 6,174,889; 6,207, 669; 6,235,741; 6,291,455; 6,294,532; 6,310,238; 6,380, 203; and 6,395,734. Specific VEGF inhibitors may comprise, for example, Su-5416, IM862, anti-VEGF monoclonal antibody (Cytran Inc.; Kirkland, Wash.), and angiozyme (Ribozyme; Boulder, Colo.). ErbB2 receptor inhibitors are disclosed in, for example, PCT International Application Publication Nos. WO 97/13760, WO 99/35132, and WO 99/35146, and U.S. Pat. Nos. 5,679,683; 5,587,458; 5,877,305; 6,207,669; and 6,391,874. Specific erbB2 receptor inhibitors may comprise, for example, GW-282974 (Glaxo Wellcome plc.), and the monoclonal antibody AR-209 (Aronex Pharmaceuticals Inc.; The Woodlands, Tex.).

Generally preferred anti-proliferative agents may comprise, for example, cytotoxic lymphocyte antigen 4 (CTLA4) antibodies, and other agents capable of blocking CTLA4; and farnesyl transferase inhibitors.

Examples of NK-1 receptor antagonists are disclosed in, for example, U.S. Pat. Nos. 5,122,525; 5,162,339; 5,232,929; 5,332,817; 5,703,240; 5,716,965; 5,719,147; 5,744,480; 5,763,699; 5,773,450; 5,807,867; 5,843,966; 5,852,038; 5,886,009; and 5,939,433.

Examples of 5HT$_{1D}$ receptor antagonists useful in the present combinations and methods are disclosed in, for example, PCT International Application Publication No. WO 94/21619, and U.S. Pat. Nos. 5,358,948; 5,510,350; 6,380,186; 6,403,592; 6,423,708; and 6,462,048.

Examples of SSRI's useful in the present combinations and methods may comprise, for example, fluoxetine (U.S. Pat. No. 4,314,081), paroxetine (U.S. Pat. No. 4,007,196), sertraline (U.S. Pat. No. 4,536,518), fluvoxamine (U.S. Pat. No. 4,085,225), venlafaxine hydrochloride (EFFEXOR®, U.S. Pat. No. 4,535,186), nefazodone hydrochloride (SERZONE®, U.S. Pat. No. 4,338,317), and bupropion hydrochloride (WELLBUTRIN®, U.S. Pat. Nos. 3,819,706 and 3,885,046).

Generally preferred anti-psychotic agents useful in the present combinations and methods may comprise, for example, ziprasidone (GEODON®, U.S. Pat. No. 5,312,925), olanzapine (U.S. Pat. No. 5,229,382), risperidone (U.S. Pat. No. 4,804,663), L-745,870, sonepiprazole, RP-62203 (fananserin), NGD-941, balaperidone, flesinoxan (U.S. Pat. No. 4,833,142), and gepirone (U.S. Pat. No. 4,423,049).

Generally preferred acetylcholinesterase inhibitors useful in the present combinations and methods may comprise, for example, donepezil (ARICEPT®, U.S. Pat. No. 4,895,841), rivastigmine (EXELON®, U.S. Pat. No. 4,948,807), metrifonate (U.S. Pat. No. 2,701,225), galanthamine, physostigmine, tacrine, huperzine, and icopezil (U.S. Pat. No. 5,538,984).

Generally preferred neuroprotectants useful in the instant combinations and methods may comprise, for example, NMDA receptor antagonists. Specific NMDA receptor antagonists comprise, for example, (1S, 2S)-1-(4-hydroxyphenyl)-2-(4-hydroxy-4-phenylpiperidin-1-yl)-1-propanol (U.S. Pat. No. 5,272,160); eliprodil (U.S. Pat. No. 4,690,931); and gavestenel (U.S. Pat. No. 5,373,018). Examples of additional NMDA antagonists are disclosed in, for example, U.S. Pat. Nos. 4,690,931; 5,185,343; 5,272,160; 5,356,905; 5,373,018; 5,744,483; 5,962,472; 6,046,213; 6,124,317; 6,124,323; 6,130,234; 6,218,404; 6,333,036; and 6,448,270; and in PCT International Application Publication Nos. WO 97/23202 and WO 98/18793.

A generally preferred potassium channel modulator comprises, for example, BMS-204352 (flindokaliner, U.S. Pat. No. 5,602,169).

The disclosures of all of the above U.S. patents are incorporated herein by reference in their entirety.

In another aspect, the invention provides methods of inhibiting glycogen synthase kinase-3 activity in a mammal in need of such inhibition which methods comprise administering a glycogen synthase kinase-3 inhibiting amount of a compound of formula (I), a prodrug thereof, or a pharmaceutically acceptable salt of the compound or prodrug; or a pharmaceutical composition comprising a compound of formula (I), a prodrug thereof, or a pharmaceutically acceptable salt of the compound or prodrug, and a pharmaceutically acceptable carrier, vehicle, or diluent.

The compounds of formula (I), the prodrugs thereof, and the pharmaceutically acceptable salts of the compounds and prodrugs, may be administered to a mammal at dosage levels in the range of from about 0.0001 mg to about 1,000 mg per day. For a normal adult human having a body mass of about 70 kg, a dosage in the range of from about 0.01 mg to about 500 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, the compounds of formula (I), the prodrugs thereof, and the pharmaceutically acceptable salts of the compounds and prodrugs, or the aforementioned combinations thereof with the amounts of one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator, are preferably administered in the form of a pharmaceutical composition comprising a pharmaceutically acceptable carrier, vehicle, or diluent. Accordingly, a compound of formula (I), a prodrug thereof, or a pharmaceutically acceptable salt of the compound or prodrug, or the aforementioned combinations, may be administered to a subject separately, or together, in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like.

Prolonged absorption of of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for xeample, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I) may be prepared according to the exemplary route disclosed in Scheme I hereinbelow, as well as by other conventional organic preparative methods known to one of ordinary skill in the relevant art. It is to be understoof that the method disclosed in Scheme 1 is intended for purposes of exemplifying the instant invention, and is not to be construed in any manner as a limitation thereon.

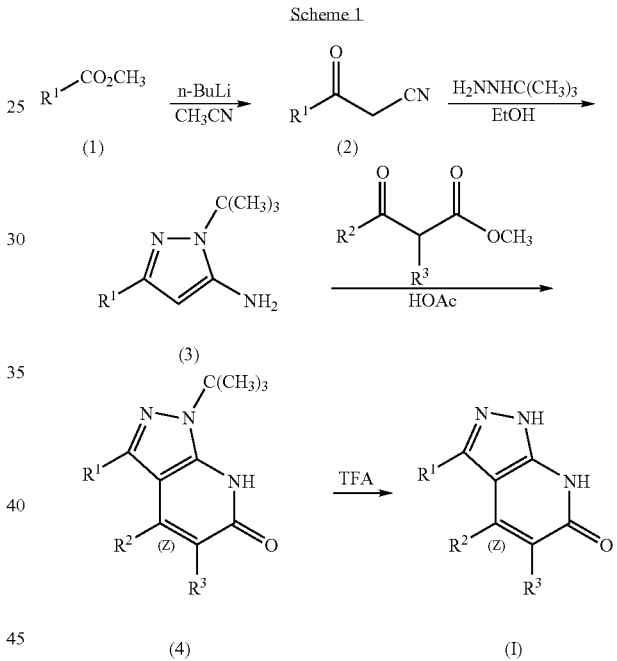

In Scheme 1, an appropriately-substituted methyl ester (1) is reacted with acetonitrile in the presence of a strong base, such as n-butyllithium, to afford α-cyanoketone (2). The reaction is normally effected in an aprotic solvent, such as tetrahydrofuran, at below ambient temperature, preferably at about −78° C. The resulting α-cyanoketone (2) is cyclocondensed with tert-butylhydrazine to afford protected aminopyrazole (3). The cyclocondensation is usually performed in a polar, protic solvent, such as ethanol at elevated temperature, preferably the reflux temperature of the solvent employed. The aminopyrazole (3) is then condensed with an appropriately-substituted ketoester to provide the dihydropyrazolo[3,4-b]pyridin-6-one derivative (4). The condensation is typically effected in a polar, protic solvent, such as glacial acetic acid, at elevated temperature, preferably between about 70-100° C. Removal of the tert-butyl protecting group, preferably with trifluoroacetic acid in a nonpolar solvent, such as dichloroethane, or neat, affords compound (I).

Preparative Experimental

Unless otherwise noted, all reagents employed were obtained commercially. Unless otherwise noted, the following experimental abbreviations have the meanings indicated:
AcOH—acetic acid
APCl—atmospheric pressure chemical ionization
n-BuLi—n-butyllithium
EtOAc—ethyl acetate
EtOH—ethanol
HPLC—high performance liquid chromatography
hr—hour(s)
LRMS—low resolution mass spectrometry
MeOH—methanol
min—minute(s)
mL—mililiter(s)
mmole—milimole(s)
MPLC—medium pressure liquid chromatography
MS—mass spectrometry
NMR—nuclear magnetic resonance
TFA—trifluoroacetic acid
THF—tetrahydrofuran
TLC—thin layer chromatogrpahy Preparation 1

3-Oxo-3-phenyl-propionitrile

To 50 mL of THF at −78° C. was added n-BuLi (58.8 mL, 147.0 mmol, 2.5 M in hexanes). After the reaction temperature equilibrated (~15 min), a solution of acetonitrile (7.7 mL, 147.0 mmol in 100 mL of THF) was added dropwise via an addition funnel over a 20 min period. The resulting milky-white slurry was allowed to stir for 1 hr before a solution of methyl benzoate (10.0 g, 73.5 mmol in 20 mL of THF) was added down the inside of the flask over a 15 min period. After 1 hr, the reaction was warmed to −45° C. (acetonitrile/$CO_2$) and allowed to stir for 2 hr. The reaction was quenched cold by the dropwise addition of 2 N HCl, pH=7 and then diluted with EtOAc. The layers were separated and the aqueous layer was extracted with $CH_2Cl_2$. The combined organic layers were dried over $MgSO_4$, filtered, and concentrated under reduced pressure to give the title compound (quantitative yield) as a colorless solid that was used without further purification. LRMS m/z (APCl) 144 (M−1); 500 MHz $^1$H NMR ($CDCl_3$) δ 7.92 (dd, J=8.4, 1.2 Hz, 2H), 7.66-7.64 (m, 1H), 7.55-7.50 (m, 2H), 4.09 (s, 2H).

Preparation 2

2-tert-Butyl-5-phenyl-2H-pyrazol-3-ylamine

To a slurry of tert-butylhydrazine hydrochloride (12.8 g, 102.9 mmol) in 350 mL of EtOH was added sodium hydroxide (3.5 g, 88.2 mmol). After 1 hr of stirring, a solution of 3-oxo-3-phenyl-propionitrile (10.6 g, 73.5 mmol, in 50 mL of EtOH) was added and the resulting slurry was heated to reflux. After 12 hr, the reaction was cooled to room temperature, filtered, and concentrated under reduced pressure. The resulting solid was washed with hexanes and dried under reduced pressure to give the title compound (13.1 g, 83% yield) as yellow-colored solid, which was used without further purification. LRMS m/z /(APCl) 216 (M+1); 500 MHz $^1$H NMR ($CD_3OD$) δ 7.67 (d, J=7.5 Hz, 2H), 7.35-7.29 (m, 2H), 7.25-7.20 (m, 1H), 5.86 (s, 1H), 1.65 (S, 9H).

Preparation 3

1-tert-Butyl-3,4-diphenyl-1,7-dihydro-pyrazolo[3,4-b]pyridin-6-one

To a stirring solution of crude 2-tert-butyl-5-phenyl-2H-pyrazol-3-ylamine (4.0 g, 18.6 mmol) in AcOH (25 mL) was added ethyl benzoylacetate (6.6 mL, 37.2 mmol). The reaction was then heated to 110° C. for 48 hr, at which time the reaction was cooled to room temperature, diluted with EtOAc, and quenched with a saturated aqueous solution of $NaHCO_3$. The organic layer was dried over $MgSO_4$, filtered through a fritted funnel, and concentrated under reduced pressure. Purification of this material was accomplished by flash chromatography, using an ISCO column (ISCO, Inc., Lincoln, Nebr.), eluting with 15% EtOAc/hexanes. The product-containing fractions were collected and concentrated under reduced pressure to give the title compound (1.0 g, 16% yield) as a tan solid. LRMS m/z (APCl) 344 (M+1).

EXAMPLE 1

3,4-Diphenyl-2,7-dihydro-pyrazolo[3,4-b]pyridin-6-one

To 1-tert-butyl-3,4-diphenyl-1,7-dihydro-pyrazolo[3,4-b]pyridin-6-one (1.0 g, 3.1 mmol) was added neat TFA (15 mL) and the resulting solution was heated to 70° C. After 18 hr, the reaction was concentrated under reduced pressure to remove TFA. The resulting tan solid was diluted with EtOAc and washed with an aqueous solution of $NaHCO_3$. The organic layer was dried over $MgSO_4$, filtered through a fritted funnel, and concentrated under reduced pressure. Purification of this material was accomplished by recrystallization from MeOH to give the title compound (0.17 g, 20% yield) as a colorless solid. LRMS m/z (APCl) 288 (M+1); 500 MHz $^1$H NMR (DMSO-D6) δ 7.29-6.92 (m, 10H), 5.90 (bs, 1H).

Preparation 4

3-Cyclobutyl-3-oxo-propionitrile

To 390 mL of THF at −78° C. was added n-BuLi (312 mL, 780 mmol, 2.5 M in hexanes). After the reaction temperature equilibrated (~15 min), a solution of acetonitrile (40.7 mL, 780.0 mmol in 200 mL of THF) was added dropwise via an addition funnel over a 20 min period. The resulting milky-white slurry was allowed to stir for 1 hr before a solution of ethyl cyclobutane carboxalate (50.0 g, 390.1 mmol in 100 mL of THF) was added down the inside of the flask over a 15 min period. After 1 hr, the reaction was warmed to −45° C. (acetonitrile/$CO_2$) and allowed to stir for 2 hr. The reaction was quenched cold by the dropwise addition of 2 N HCl (pH=7) and then diluted with EtOAc. The layers were separated and the aqueous layer was extracted with $CH_2Cl_2$. The combined organic layers were dried over $MgSO_4$, filtered, and concentrated under reduced pressure to give the title compound (quantitative yield) as a colorless oil that was used without further purification. LRMS m/z (APCl) 121 (M−1).

Preparation 5

2-tert-Butyl-5-cyclobutyl-2H-pyrazol-3-ylamine

To a slurry of tert-butylhydrazine hydrochloride (68 g, 546 mmol) in 1 L of EtOH was added sodium hydroxide (18.7 g, 468.1 mmol). After 1 hr of stirring, a solution of crude 3-cyclobutyl-3-oxo-propionitrile (390.1 mmol, in 100 mL of EtOH) was added, and the resulting slurry was heated to reflux. After 12 hr, the reaction was cooled to room temperature, filtered, and concentrated under reduced pressure. The slurry was diluted with EtOAc and then washed with a saturated solution of NaHCO$_3$. The organic layer was dried over MgSO$_4$, filtered through a fritted funnel, and concentrated under reduced pressure. The product was isolated by trituration with 25% EtOAc/hexanes. After several trituration cycles, the title compound (60 g, 80% yield) was collected as a colorless solid, which was used without further purification. LRMS m/z (APCl) 194 (M+1).

Preparation 6

1-tert-Butyl-3-cyclobutyl4-methyl-1,7-dihydro-Pyrazolo[3,4-b]pyridin6-one

To a stirring solution of crude 2-tert-butyl-5-cyclobutyl-2H-pyrazol-3-ylamine (1.0 g, 5.2 mmol) in AcOH (10 mL) was added methyl acetoacetate (1.1 mL, 10.4 mmol). The reaction was then heated to 105° C. for 24 hr, at which time the reaction was cooled to room temperature, concentrated under reduced pressure to remove AcOH, diluted with EtOAc, and quenched with a saturated aqueous solution of NaHCO$_3$. The organic layer was dried over MgSO$_4$, filtered through a frilted funnel, and concentrated under reduced pressure. Purification of the resulting material was accomplished by trituration with hexanes. The product was collected and dried under reduced pressure to give the title compound (0.7 g, 52% yield) as a tan solid. LRMS m/z (APCl) 259.3 (M+1); 500 MHz $^1$H NMR (CD$_3$OD) δ 6.09 (1, 1H), 3.83 (dddd, J=8.7, 8.7, 8.7, 8.7 Hz, 1H), 2.49-2.28 (m, 4H), 2.42 (d, J=0.8 Hz, 3H), 2.11-2.01 (m, 1H), 1.94-1.86 (m, 1H), 1.71 (s, 9H).

EXAMPLE 2

3-Cyclobutyl-4-methyl-2,7-dihydro-pyrazolo[3,4-b]pyridin-6-one hydrochloride

To 1-tert-butyl-3-cyclobutyl-4-methyl-1,7-dihydro-pyrazolo[3,4-b]pyridin-6-one (1.0 g, 3.8 mmol) was added neat TFA (6 mL) and the resulting solution was heated to 65° C. After 5 hr, the reaction was concentrated under reduced pressure to remove TFA. The resulting product was diluted with EtOAc and a solution of HCl (9 mL, 1M in Et$_2$O) was added. The resulting solid was collected and dried under reduced pressure to give the title hydrochloride salt (0.79 g, 87% yield) as a colorless solid. LRMS m/z (APCl) 204 (M+1); 500 MHz $^1$H NMR (CD$_3$OD) δ 6.48 (s, 1H), 4.14 (dddd, J=8.7, 8.7, 8.7, 8.7 Hz, 1H), 2.67 (s, 3H), 2.55-2.37 (m, 4H), 2.26-2.16 (m, 1H), 2.03-1.95 (m, 1H); 125 MHz $^{13}$C NMR (CD$_3$OD) d 163.5, 156.1, 146.9, 145.9, 107.9, 107.0, 32.0, 28.2, 19.4, 18.0.

Preparation 7

1-tert-Butyl-3-cyclobutyl-5-phenyl-1,7-dihydro-pyrazolo[3,4-b]pyridin-6-one

To a stirring solution of crude 2-tert-butyl-5-cyclobutyl-2H-pyrazol-3-ylamine (1.0 g, 5.2 mmol) in AcOH (5 mL) was added 3-oxo-2-phenyl-propionic acid ethyl ester (1.0 g, 5.2 mmol). The reaction was then heated to 110° C. for 18 hr, at which time the reaction was cooled to room temperature, concentrated under reduced pressure to remove HOAc, diluted with EtOAc, and quenched with a saturated aqueous solution of NaHCO$_3$. The organic layer was dried over MgSO$_4$, filtered through a fritted funnel, and concentrated under reduced pressure. Purification of the resulting material was accomplished by flash chromatography with a Biotage® 35L column (A Dynax Corp., Charlottesville, Va.), eluting with a gradient of 5%, 10%, 20% EtOAc/hexanes. The product was collected and concentrated under reduced pressure to give the title compound (15 mg, 9% yield). LRMS m/z (APCl) 322 (M+1).

EXAMPLE 3

3-Cyclobutyl-5-phenyl-2,7-dihydro-pyrazolo[3,4-b]pyridin-6-one hydrochloride

To 1-tert-butyl-3-cyclobutyl-5-phenyl-1,7-dihydro-pyrazolo[3,4-b]pyridin-6-one (15 mg, 0.047 mmol) was added neat TFA (1.0 mL) and reaction was heated to 70° C. After 18 hr, the reaction was cooled to room temperature and concentrated under reduced pressure. The resulting product was dissolved in EtOAc and a solution of HCl (47 uL, 1M Et$_2$O) was added. The resulting product was filtered and washed with hexanes to give the title hydrochloride salt (11 mg, 77% yield) as a tan solid. LRMS m/z (APCl) 266 (M+1); 500 MHz $^1$H NMR (CD$_3$OD) δ 7.91 (s, 1H), 7.57 (d, J=7.0 Hz, 2H), 7.41-7.30 (m, 3H), 3.92 (dddd, J=9.1, 9.1, 9.1, 9.1 Hz, 1H), 2.52-2.38 (m, 4H), 2.23-2.11 (m, 1H), 2.04-1.97 (m, 1H).

Preparation 8

1-tert-Butyl-3-cyclobutyl-4-trifluoromethyl-1,7-dihydro-pyrazolo[3,4-b]pyridin-6-one To a stirring solution of crude 2-tert-butyl-5-cyclobutyl-2H-pyrazol-3-ylamine (2.0 g, 10.4 mmol) in AcOH (10 mL) was added 4,4,4-trifluoro-3-oxo-butyric acid methyl ester (3.5 g, 20.7 mmol). The reaction was then heated to 110° C. for 18 hr, at which time the reaction was cooled to room temperature, concentrated under reduced pressure, diluted with EtOAc, and quenched with a saturated aqueous solution of NaHCO$_3$. The organic layer was dried over MgSO$_4$, filtered through a fritted funnel, and concentrated under reduced pressure to give the title compound (3.2 g, quantitative yield). This material was used without further purification. LRMS m/z (APCl) 314 (M+1); 500 MHz $^1$H NMR (CDCl$_3$) δ 6.66 (s, 1H), 3.78 (dddd, J=8.3, 8.3, 8.3, 8.3 Hz, 1H), 2.49-2.39 (m, 2H), 2.34-2.26 (m, 2H), 2.06-1.85 (m, 2H), 1.75 (s, 9H).

EXAMPLE 4

3-Cyclobutyl4-trifluoromethyl-2,7-dihydro-pyrazolo[3,4-b]pyridin-6-one

To 1-tert-butyl-3-cyclobutyl-4-trifluoromethyl-1,7-dihydro-pyrazolo[3,4-b]pyridin-6-one (200 mg, 0.64 mmol) was added neat TFA (2.0 mL) and reaction was heated to 70° C. After 18 hr, the reaction was cooled to room temperature and concentrated under reduced pressure. The resulting product was dissolved in EtOAc and a solution of HCl (320 uL, 2M Et$_2$O) was added, followed by isopropyl ether. The product was filtered and washed with hexanes to give the title hydrochloride salt (138 mg, 74% yield) as a colorless solid. LRMS m/z (APCl) 258 (M+1); 500 MHz $^1$H NMR (CD$_3$OD) δ 6.53 (s, 1H), 3.90 (dddd, J=8.7, 8.7, 8.7, 8.7 Hz, 1H), 2.41-2.30 (m, 4H), 2.16-2.04 (m, 1H), 1.98-1.91 (m, 1H).

Preparation 9

1-tert-Butyl-3-cyclobutyl-4phenyl-1,7-dihydro-pyrazolo[3,4-b]pyridin-6-one

To a stirring solution of crude 2-tert-butyl-5-cyclobutyl-2H-pyrazol-3-ylamine (4.0 g, 20.7 mmol) in AcOH (20 mL) was added 3-oxo-3-phenyl-propionic acid ethyl ester (3.5 g, 20.7 mmol). The reaction was then heated to 110° C. for 14 hr, at which time the reaction was cooled to room temperature and concentrated under reduced pressure. Purification of the resulting material was accomplished by flash chromatography using a 75 g short Biotageo column, eluting with a gradient of 5%, 10% EtOAc/hexanes. The product-containing fractions were collected and concentrated to give the title compound (1.0 g, 15% yield) as a colorless solid. $R_f$=0.31 (20% EtOAc/hexanes); LRMS m/z (APCl) 322 (M+1); 500 MHz $^1$H NMR (CDCl$_3$) δ 7.46-7.44 (m, 3H), 7.38-7.36 (m, 2H), 6.17 (s, 1H), 3.16 (dddd, J=7.9, 7.9, 7.9, 7.9 Hz, 1H), 2.17-2.11 (m, 2H), 1.76 (s, 9H), 1.71-1.67 (m, 4H); 125 MHz $^{13}$C NMR (CDCl$_3$) δ 163.1, 151.0, 147.5, 141.8, 138.5, 128.9, 128.4, 128.2, 112.5, 110.6, 105.7, 59.7, 34.2, 29.2, 27.6, 18.4.

EXAMPLE 5

3-Cyclobutyl-4-phenyl-2,7-dihydro-pyrazolo[3,4-b]yridin-6-one hydrochloride

To 1-tert-butyl-3-cyclobutyl-4-phenyl-1,7-dihydro-pyrazolo[3,4-b]pyridin-6-one (210 mg, 0.64 mmol) was added neat TFA (4.0 mL) and reaction was heated to 69° C. After 24 hr, the reaction was cooled to room temperature and concentrated under reduced pressure. The resulting product was dissolved in EtOAc, and a solution of HCl (700 uL, 2M Et$_2$O) was added, followed by isopropyl ether. The product was filtered and washed with hexanes to give the title hydrochloride salt (175 mg, 61% yield) as a light yellow solid. LRMS m/z (APCl) 266 (M+1); 500 MHz $^1$H NMR (DMSO-D6) δ 7.46 (bs, 3H), 7.39 (bs, 2H), 5.86 (s, 1H), 3.18 (dddd, J=8.3, 8.3, 8.3, 8.3 Hz, 1H), 2.05-2.00 (m, 2H), 1.78-1.58 (m, 4).

Preparation 10

1-tert-Butyl-3-cyclobutyl-1,7-dihydro-pyrazolo[3,4-b]pyridin-6-one

To 2-tert-butyl-5-cyclobutyl-2H-pyrazol-3-ylamine (5.0 g, 25.9 mmol) in AcOH (25 mL) was added methyl dimethoxypropionate (7.4 mL, 51.8 mmol), and then the reaction was heated to 110° C. After 24 hr, the reaction mixture was cooled to room temperature, and concentrated to a viscous oil that was treated with EtOAc. The organic layer was washed with aqueous NaHCO$_3$ dried over MgSO$_4$, filtered, and concentrated under reduced pressure. Purification of this material was accomplished by MPLC using a 45L Biotage® column eluting with 20% EtOAc/hexanes. The product-containing fractions were collected and concentrated under reduced pressure, and the resulting solid was washed with hexanes and dried to afford the title compound (2.0 g, 32% yield) as a colorless solid. $R_f$=0.33 (10% MeOH/CH$_2$Cl$_2$); 500 MHz $^1$H NMR (CDCl$_3$) d 7.72 (d, J=9.1 Hz, 1H), 6.26 (d, J=9.1 Hz, 1H), 3.68 (dddd, J=8.7, 8.7, 8.7, 8.7 Hz, 1H), 2.46-2.32 (m, 4H), 2.14-1.89 (m, 2H), 1.71 (s, 9H); LRMS m/z (APCl$^+$) 246 (M+1).

Preparation 11

5-Bromo-1-tert-butyl-3-cyclobutyl-1,7-dihydro-pyrazolo[3,4-b]pyridin-6-one

To a stirring solution of 1-tert-butyl-3-cyclobutyl-1,7-dihydro-pyrazolo[3,4-b]pyridin-6-one (1.0 g, 4.1 mmol) in AcOH (10 mL) was added bromine (236 uL, 4.6 mmol) dropwise. After 15 min, the resulting solid was collected and washed with hexanes. The solution was diluted with EtOAc and washed with a saturated aqueous solution of NaHCO$_3$. The organic layer was dried over MgSO$_4$ and concentrated under reduced pressure. Purification of the resulting material was accomplished by flash chromatography, using a Biotage® column, eluting with a gradient of 10%, 20% EtOAc/hexanes. The product-containing fractions were collected and concentrated to give the title compound (220 mg, 16% yield) as a tan solid. LRMS m/z (APCl) 322, 324 (M−1); 500 MHz $^1$H NMR (CDCl$_3$) δ 12.5 (bs, 1H), 8.09 (s, 1H), 3.66 (dddd, J=8.7, 8.7, 8.7, 8.7 Hz, 1H), 2.45-2.34 (m, 4H), 2.15-1.92 (m, 2H), 1.76 (s, 9H).

Preparation 12

1-tert-Butyl-3-cyclobutyl-5-(3,5-dichloro-phenyl)-1,7-dihydro-pyrazolo[3,4-b]pyridin-6-one To a stirring solution of 5-bromo-1-tert-butyl-3-cyclobutyl-1,7-dihydro-pyrazolo[3,4-b]pyridin-6-one (50.0 mg, 0.15 mmol) in dimethoxyethane (1.5 mL) was added 3,5-dichlorophenyl-boronic acid (32.6 mg, 0.17 mmol), followed by cesium fluoride (51.9 mg, 0.34 mmol), and Pd(PPh$_3$)$_4$ (catalytic amount, 0.005 mmol). The reaction mixture was heated to reflux. After 3 hr, additional amounts of 3,5-dichlorophenyl-boronic acid (32.6 mg, 0.17 mmol), cesium fluoride (51.9 mg, 0.34 mmol), and Pd(PPh$_3$)$_4$ (catalytic amount, 0.005 mmol) were added. After a total of 18 hr, the reaction was cooled to room temperature, diluted with CH$_2$Cl$_2$ and washed with water. The organic layer was dried over MgSO$_4$, filtered through a fritted funnel, and concentrated under reduced pressure. Purification of the resulting material was accomplished by flash chromatography with a Biotage® column, eluting with 5% EtOAc/toluene. The product-containing fractions were collected and concentrated to give the title compound (7.0 mg, 12% yield). LRMS m/z (APCl) 390. 392(M+1).

EXAMPLE 6

3-Cyclobutyl-5-(3,5-dichloro-phenyl)-2,7-dihydro-pyrazolo[3,4-b]pyridin-6-one hydrochloride To 1-tert-butyl-3-cyclobutyl-5-(3,5-dichloro-phenyl)-1,7-dihydro-pyrazolo[3,4-b]pyridin-6-one (7 mg, 0.02 mmol) was added anisole (200 uL) and TFA (2.0 mL) and the reaction mixture was heated to 70° C. After 18 hr, the reaction was cooled to room temperature and concentrated under reduced pressure. The resulting product was dissolved in EtOAc and a solution of HCl (15 uL, 2M Et$_2$O) was added, followed by isopropyl ether. The product was filtered and washed with hexanes to give the title hydrochloride salt (5.1 mg, 77% yield). LRMS m/z (APCl) 322, 324 (M−1); 500 MHz $^1$H NMR (CDCl$_3$) δ 8.00 (s, 1H), 7.61 (d, J=1.6, 1.6 Hz, 2H), 7.40 (dd, J=1.6, 1.6, 1H), 3.93 (dddd, J=9.1, 9.1, 9.1, 9.1 Hz, 1H), 2.49-2.37 (m, 4H), 2.23-2.11 (m, 1H) 2.03-1.96 (m, 1H).

Preparation 13

1-tert-Butyl-5-cyclobutyl-4-(2,4,5-trifluoro-phenyl)-1,7-dihydro-pyrazolo[3,4-b]pyridin-6-one To a stirring solution of crude 2-tert-butyl-5-cyclobutyl-2H-pyrazol-3-ylamine (0.5 g, 2.6 mmol) in AcOH (10 mL) was added 3-oxo-3-(2,4,5-trifluoro-phenyl)-propionic acid ethyl ester (1.3 g, 5.1 mmol). The reaction mixture was then heated to 110° C. for 14 hr, at which time the reaction was cooled to room temperature and concentrated under reduced pressure. Purification of this material was accomplished by flash chromatography using a 35 g ISCO column, eluting with 20% EtOAc/hexanes. The product-containing fractions were collected and concentrated to give the title compound. LRMS m/z (APCl) 376 (M+1).

EXAMPLE 7

3-Cyclobutyl-4-(2,4,5-trifluoro-phenyl)-2,7-dihydro-pyrazolo[3,4-b]pyridin-6-one hydrochloride To 1-tert-butyl-5-cyclobutyl-4-(2,4,5-trifluoro-phenyl)-1,7-dihydro-[3,4-b]pyrindin-6-one (370 mg, 0.99 mmol) was added anisole (500 uL) and neat TFA (2.0 mL) and reaction was heated to 70° C. After 12 hr, the reaction mixture was cooled to room temperature and concentrated under reduced pressure. The resulting product was dissolved in EtOAc and washed with 1N NaOH. The organic layer was dried over $MgSO_4$, filtered through a fritted funnel, and concentrated under reduced pressure. The resulting product was then taken up in EtOAc and a solution of HCl (1 mL, 2M $Et_2O$) was added, followed by isopropyl ether. The product was filtered off and washed with hexanes to give the title hydrochloride salt (246 mg, 69% yield) as a colorless solid. LRMS m/z (APCl) 320 (M−1); 500 MHz $^1$H NMR (DMSO-D6) δ 7.77-7.66 (m, 2H), 5.96 (s, 1H), 3.08 (dddd, J=8.3, 8.3, 8.3, 8.3 Hz, 1H), 2.13-2.07 (m, 2H), 1.80-1.66 (m, 4H).

Biological Methodologies

GSK-3 Inhibition

The specific activities of the compounds of formula (I) in inhibiting GSK-3 can be determined in both cell-free and cell-based assays, both of which have been previously described in the relevant art. See, for example, U.S. Pat. Nos. 6,417,185 and 6,489,344, the disclosures of which are incorporated herein by reference in their entirety.

A cell-free assay can be generally carried out by incubating GSK-3 with a peptide substrate, radiolabeled ATP (e.g., for example, $\gamma^{33}$P- or $\gamma^{32}$P-ATP, both of which are available from Amersham; Arlington Heights, Ill.), magnesium ions, and the compound to be assayed. The mixture is incubated for a period of time to allow incorporation of radiolabeled phosphate into the peptide substrate by GSK-3 activity. The reaction mixture is then washed to remove unreacted radiolabeled ATP, typically after first transferring all or a portion of the enzyme reaction mixture to a well that contains a uniform amount of a ligand capable of binding to the peptide substrate. The amount of $\gamma^{33}$P or $\gamma^{32}$P remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, described in Wang, et al., Anal. Biochem., 220, 397402 (1994). Purified GSK-3 for an assay may, for example, be obtained from cells transfected with a human GSK-3β expression plasmid as described in, for example, Stambolic, et al., Current Biology, 6, 1664-1668 (1996).

Another example of a GSK-3 assay, similar to the one described hereinabove, is as follows: enzyme activities are assayed as the incorporation of $^{33}$P from gamma phosphate of $^{33}$P-ATP (Amersham; Arlington Heights, Ill.; catalog #AH-9968) into biotinylated peptide substrate PKTP-KKAKKL. Reactions are carried out in a buffer containing 50 mM Tris-HCl, pH 8.0; 10 mM $MgCl_2$, 0.1 mM $Na_3VO_4$, and 1 mM DTT. The final concentration of ATP is 0.5 μM (final specific radioactivity of 4 μCi/nmol), and the final concentration of substrate is 0.75 μM. Reactions, initiated by the addition of enzyme, are carried out at room temperature for about 60 min. Reactions are stopped by addition of 0.6 volume of buffer containing (final concentrations): 2.5 mM EDTA, 0.05% Triton-X 100, 100 μM ATP, and 1.25 mg/ml streptavidin-coated SPA beads (Amersham; Arlington Heights, Ill.; catalog #RPNQ0007). Radioactivity associated with the beads is then quantified by scintillation counting.

A generally preferred GSK-3 testing assay, similar to the one described hereinabove, is as follows: enzyme activities are assayed as the incorporation of $^{33}$P from the gamma phosphate of $^{33}$P-ATP (Amersham; Arlington Heights, Ill.; catalog #AH-9968) into biotinylated peptide substrate Biotin-SRHSSPHQpSEDEEE-OH (AnaSpec Inc., San Jose, Calif.). The reactions are carried out in a buffer containing 8 mM MOPS; 10 mM $Mg(OAc)_2$, 0.2 mM EDTA (pH 7.0), and 1 mM DTT. The final concentration of ATP is 2.0 μM (final specific radioactivity of 4 μCi/nmol), and the final concentration of substrate is 1.0 μM. The reactions, initiated by the addition of enzyme, are carried out at room temperature for about 75 minutes. The reactions are stopped by addition of 0.6 volume of buffer containing (final concentrations): .05 mM EDTA, 0.1% Triton-X 100, 100 μM ATP, and 2.5 mg/ml streptavidin-coated SPA beads. Radioactivity associated with the beads is then quantified by standard scintillation counting.

The compounds of formula (I) generally exhibit inhibitory activity, expressed as $IC_{50}$'s, against GSK-3 that are <10,000 nM. Generally preferred compounds have $IC_{50}$'s<200 nM. For example, the compound 3-cyclobutyl-4-phenyl-2,7-dihydro-pyrazolo[3,4-b]pyridin-6-one has an $IC_{50}$ of 36 nM.

What is claimed is:
1. A compound of formula (I)

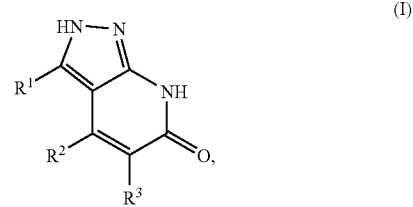

or a stereoisomer thereof, or a pharmaceutically acceptable salt of said compound or stereoisomer, wherein:
$R^1$ and $R^2$ are, independently, hydrogen; —($C_1$-$C_8$)alkyl; —($C_1$-$C_8$)alkoxy; —($C_3$-$C_{11}$)cycloalkyl; heterocycloalkyl; aryl; or heteroaryl; and
$R^3$ is hydrogen; —($C_1$-$C_8$)alkyl; —($C_1$-$C_8$)alkoxy; or —($C_3$-$C_{11}$)cycloalkyl;

R$^1$ and R$^2$ are, independently, hydrogen; —(C$_1$-C$_8$)alkyl; —(C$_1$-C$_8$)alkoxy; —(C$_3$-C$_{11}$)cycloalkyl; heterocycloalkyl; aryl; or heteroaryl; and R$^3$ is hydrogen; —(C$_1$-C$_8$)alkyl; —(C$_1$-C$_8$)alkoxy; or —(C$_3$-C$_{11}$)cycloalkyl;

wherein each R$^1$, R$^2$, and R$^3$ is optionally, and independently, substituted with from one to six of: (A) halogen; (B) aryl, optionally substituted with from one to three of: (i) —OH; (ii) —CN; (iii) halogen; (iv) heteroaryl; (v) —CH$_2$OR$^4$; or (vi) —CH$_2$NR$^4$R$^5$; (C) heteroaryl; (D) —NO$_2$; (E) —CN; (F) —(C$_1$-C$_8$)alkyl, optionally substituted with from one to three halogen atoms; (G) —(C$_1$-C$_8$)thioalkoxy; (H) —NR$^4$R$^5$; (I) —NR$^4$C(=O)R$^5$; (J) —NR$^4$C(=O)NR$^4$R$^5$; (K) —NR$^4$(SO$_2$)R$^5$; (L) —NR$^4$(SO$_2$)NR$^4$R$^5$; (M) —OR$^4$; (N) —OC(=O)R$^4$; (O) —OC(=O)OR$^4$; (P) —C(=O)OR$^4$; (Q) —C(=O)R$^4$; (R) —C(=O)NR$^4$R$^5$; (S) —OC(=O)NR$^4$R$^5$; (T) —OC(=O)SR$^4$; (U) —SR$^4$; (V) —S(=O)R$^4$; (W) —SO$_2$R$^4$; or (X) —SO$_2$R$^4$R$^5$; wherein:

R$^4$ and R$^5$ are, independently, hydrogen; aryl, optionally substituted with from one to three of: halogen; —OH; —(C$_1$-C$_8$)alkyl, optionally substituted with aryl; or —(C$_3$-C$_{11}$)cycloalkyl;

provided that when R$^3$ is hydrogen: (1) R$^1$ is not hydrogen, and R$^2$ is not hydrogen or methyl; (2) R$^1$ and R$^2$ are not both methyl; or (3) R$^1$ is not hydrogen or phenyl, and R$^2$ is not trifluoromethyl.

2. A compound of claim 1, wherein:

R$^1$ is —(C$_1$-C$_5$)alkyl or —(C$_3$-C$_6$)cycloalkyl;

R$^2$ is hydrogen; —(C$_1$-C$_8$)alkyl; —(C$_1$-C$_8$)alkoxy; —(C$_3$-C$_9$)cycloalkyl; heterocycloalkyl; aryl; or heteroaryl; and R$^3$ is hydrogen; —(C$_1$-C$_3$)alkyl; —(C$_1$-C$_6$)alkoxy; or —(C$_3$-C$_6$)cycloalkyl;

wherein each R$^1$, R$^2$, and R$^3$ is optionally, and independently, substituted with from one to six of: (A) halogen; (B) aryl, optionally substituted with from one to three of: (i) —OH; (ii) —CN; (iii) halogen; (iv) heteroaryl; (v) —CH$_2$OR$^4$; or (vi) —CH$_2$NR$^4$R$^5$; (C) heteroaryl; (D) —NO$_2$; (E) —CN; (F) —(C$_1$-C$_8$)alkyl, optionally substituted with from one to three fluorine atoms; (G) —(C$_1$-C$_8$)thioalkoxy; (H) —NR$^4$R$^5$; (I) —NR$^4$C(=O)R$^5$; (J) —NR$^4$C(=O)NR$^4$R$^5$; (K) —NR$^4$(SO$_2$)R$^5$; (L) —NR$^4$(SO$_2$)NR$^4$R$^5$; (M) —OR$^4$; (N) —OC(=O)R$^4$; (O) —OC(=O)OR$^4$; (P) —C(=O)OR$^4$; (Q) —C(=O)R$^4$; (R) —C(=O)NR$^4$R$^5$; (S) —OC(=O)NR$^4$R$^5$; (T) —OC(=O)SR$^4$; (U) —SR$^4$; (V) —S(=O)R$^4$; (W) —SO$_2$R$^4$; or (X) —SO$_2$R$^4$R$^5$.

3. A compound of claim 1, wherein:

R$^1$ is —(C$_1$-C$_5$)alkyl or —(C$_3$-C$_6$)cycloalkyl;

R$^2$ is hydrogen; —(C$_1$-C$_8$)alkyl; —(C$_1$-C$_8$)alkoxy; —(C$_3$-C$_9$)cycloalkyl; heterocycloalkyl; aryl; or heteroaryl; and R$^3$ is hydrogen;

wherein each R$^1$ or R$^2$ is optionally, and independently, substituted with from one to six of: (A) Cl or Fl; (B) aryl, optionally substituted with from one to three of: (i) —OH; (ii) —CN; (iii) halogen; (iv) heteroaryl; (v) —CH$_2$OR$^4$; or (vi) —CH$_2$NR$^4$R$^5$; (C) heteroaryl; (E) —CN; (F) —CF$_3$; (G) —(C$_1$-C$_8$)thioalkoxy; (H) —NR$^4$R$^5$; (I) —NR$^4$C(=O)R$^5$; (J) —NR$^4$C(=O)NR$^4$R$^5$; (K) —NR$^4$(SO$_2$)R$^5$; (L) —NR$^4$(SO$_2$)NR$^4$R$^5$; (M) —OR$^4$; (N) —OC(=O)R$^4$; (O) —OC(=O)OR$^4$; (P) —C(=O)OR$^4$; (Q) —C(=O)R$^4$; (R) —C(=O)NR$^4$R$^5$; (S) —OC(=O)NR$^4$R$^5$; (T) —OC(=O)SR$^4$; (W) —SO$_2$R$^4$; or (X) —SO$_2$R$^4$R$^5$.

4. A compound of claim 1 selected from the group consisting of:

3,4-diphenyl-2,7-dihydro-pyrazolo[3,4-b]pyridin-6-one;

3-cyclobutyl-4-phenyl-2,7-dihydro-pyrazolo[3,4-b]pyridin-6-one; and 3-cyclobutyl-4-(2,4,5-trifluoro-phenyl)-2,7-dihydro-pyrazolo[3,4-b]pyridin-6-one, or a stereoisomer thereof, or a pharmaceutically acceptable salt of said compound or stereoisomer.

5. A pharmaceutical composition comprising:

(a) a compound of claim 1 or a stereoisomer thereof, or a pharmaceutically acceptable salt of said compound or a stereoisomer thereof.

6. A pharmaceutical composition comprising:

(a) a compound of claim 1 or a stereoisomer thereof, or a pharmaceutically acceptable salt of said compound or a stereoisomer thereof.

* * * * *